(12) United States Patent
Reed et al.

(10) Patent No.: US 8,466,687 B2
(45) Date of Patent: Jun. 18, 2013

(54) SYSTEM AND METHOD FOR DETECTING DEFECTS

(75) Inventors: C. Christopher Reed, El Segundo, CA (US); Tom R. Newbauer, Claremont, CA (US); Richard Briët, Cypress, CA (US)

(73) Assignee: The Aerospace Corporation, El Segundo, CA (US)

( * ) Notice: Subject to any disclaimer, the term of this patent is extended or adjusted under 35 U.S.C. 154(b) by 323 days.

(21) Appl. No.: 12/924,099

(22) Filed: Sep. 20, 2010

(65) Prior Publication Data

US 2012/0068716 A1    Mar. 22, 2012

(51) Int. Cl.
*G01N 27/61* (2006.01)

(52) U.S. Cl.
USPC .......................................... 324/454; 324/713

(58) Field of Classification Search
USPC .......................................... 324/713–718, 454
See application file for complete search history.

(56) References Cited

U.S. PATENT DOCUMENTS

| | | | | |
|---|---|---|---|---|
| 3,983,401 | A | * | 9/1976 | Livesay ...................... 250/492.2 |
| 7,358,748 | B1 | * | 4/2008 | Miller et al. .................. 324/716 |
| 2007/0077362 | A1 | * | 4/2007 | Ruzzo et al. .................. 427/446 |

* cited by examiner

*Primary Examiner* — Vincent Q Nguyen
(74) *Attorney, Agent, or Firm* — K&L Gates LLP

(57) ABSTRACT

A system including a charge source and at least one voltage measurement device is disclosed. The charge source is for generating a charging environment to produce at least one of a voltage profile and a current on an area of dielectric material disposed over a conductive substrate. The area of dielectric material includes a first area containing a subsurface defect. The area of dielectric material also includes a second area that is defect-free. The at least one voltage measurement device is for outputting voltage measurements at different positions over the area of dielectric material. The voltage measurements over the first area differ from voltage measurements over the second area to define a voltage differential.

25 Claims, 14 Drawing Sheets

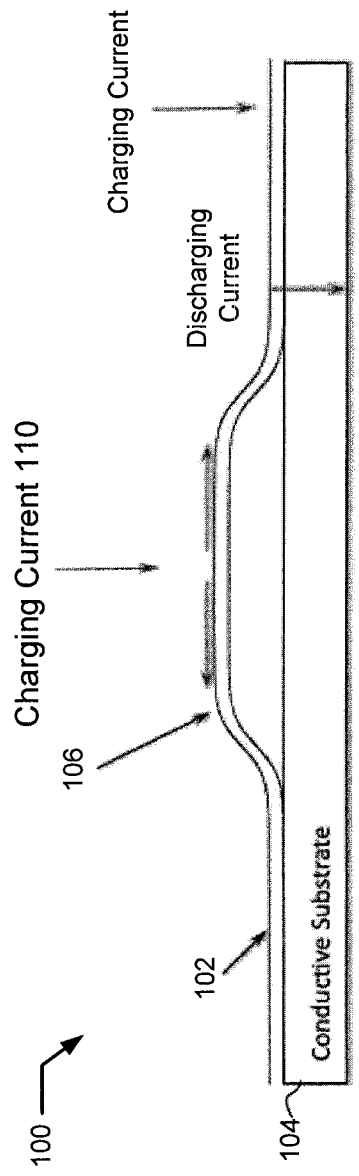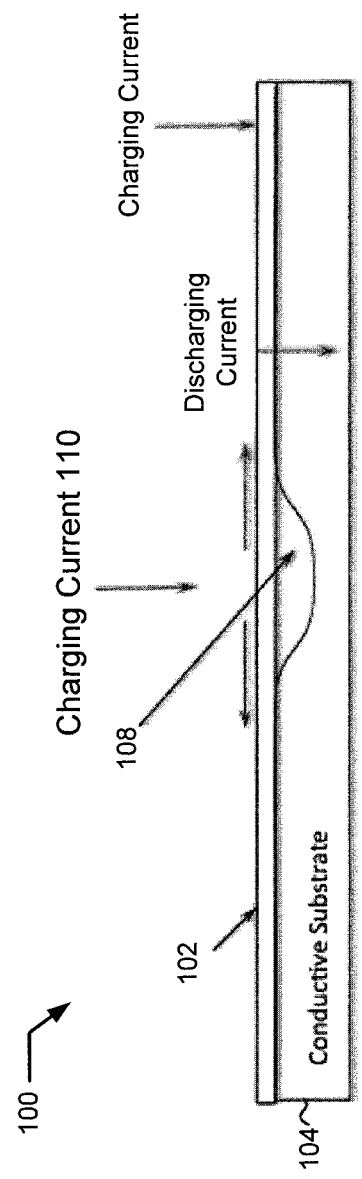

SYSTEM AND METHOD FOR DETECTING DEFECTS

STATEMENT REGARDING FEDERALLY SPONSORED RESEARCH AND DEVELOPMENT

This invention was made with government support under Contract No. FA8802-09-C-0001 awarded by the United States Air Force. The government has certain rights in the invention.

BACKGROUND

During or after the manufacture of an article, defects that are difficult to detect based on a visual inspection of the article's exterior may occur. In some cases, the defects are present under an exterior surface of the article, such as under a surface coating, for example. Subsurface defects and other types of hard-to-observe flaws may have a number of undesirable consequences. In space systems, for example, subsurface defects may degrade thermal control surfaces due to comprised paint, increase the likelihood of electrostatic discharges (ESD) on satellites, diminish ESD mitigation on solar cells due to coating loss, permit contamination of optical components due to surface peeling and flaking, and cause rocket motor failure due to delamination of composite materials.

The advantages of non-destructive evaluation and testing (NDET) techniques to detect subsurface defects and other types of flaws are known. Thermography is one example of a NDET technique for detecting subsurface defects. Thermographic techniques generally involve subjecting a test article to a thermal pulse (e.g., from a flash bulb) followed immediately by an examination/evaluation of surface temperature differences using an infrared camera. One advantage of thermography is that it provides nearly instantaneous results. A possible disadvantage is that the thermal pulse may cause new defects if the test article contains volatile materials in microcracks, or if the composition of the test article includes materials with mismatched coefficients of thermal expansion. More benign NDET techniques are desirable.

SUMMARY

Various aspects of a non-destructive evaluation and testing system including a charge source and at least one voltage measurement device are disclosed. The charge source is for generating a charging environment to produce at least one of a voltage profile and a current on an area of dielectric material disposed over a conductive substrate. The area of dielectric material includes a first area containing a subsurface defect. The area of dielectric material also includes a second area that is defect-free. The at least one voltage measurement device is for outputting voltage measurements at different positions over the area of dielectric material. The voltage measurements over the first area differ from voltage measurements over the second area to define a voltage differential.

DESCRIPTION OF THE FIGURES

Various embodiments of the present invention are described herein by way of example in conjunction with the following figures, wherein:

FIGS. 1A and 1B illustrate a dielectric-coated conductive substrate in a charging environment;

DESCRIPTION

Figure 2:
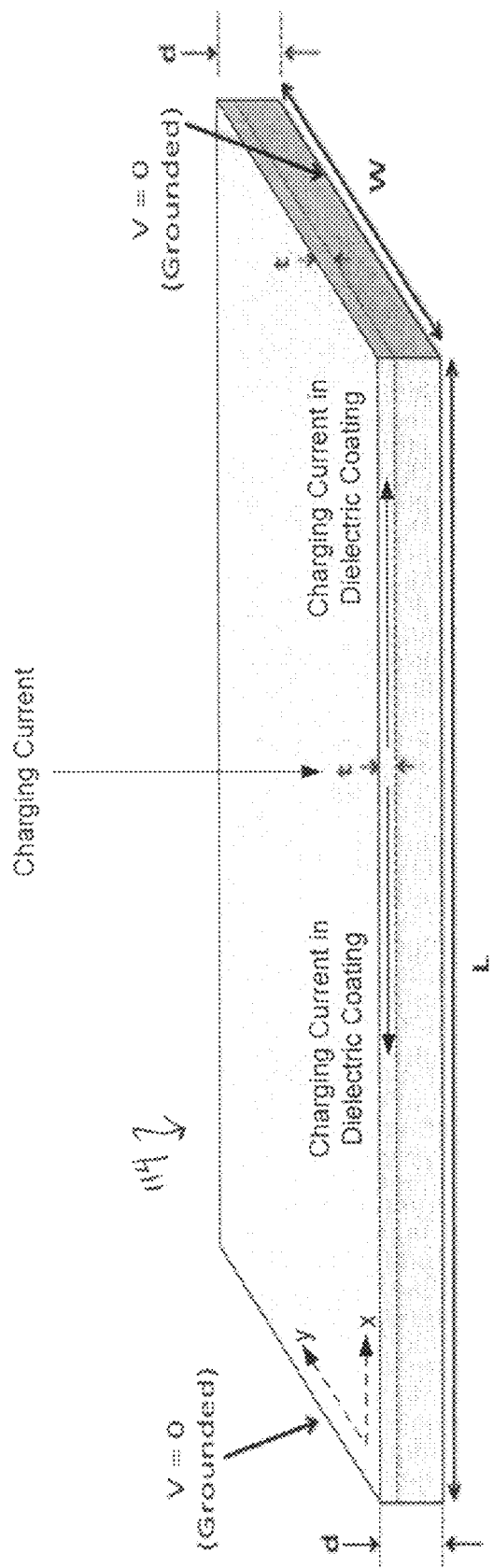
FIGS. 2 and 4 illustrate the geometry and boundary conditions of dielectric coatings on a conductive substrate according to various embodiments.

Embodiments of the present application are directed to electrostatic non-destructive evaluation and testing (ES-NDET) systems and methods for detecting defects, such as subsurface defects in dielectric-coated conductive substrates. The systems and methods may use a controlled charging environment to produce a voltage on a surface area of an article containing a subsurface defect that is different than a voltage produced by the charging environment on a defect-free surface area of the article. The defect may be detected by detecting the resulting voltage change or difference (e.g., a voltage differential) between the defect-containing surface area and the defect-free surface area using a voltage measurement device, such as a non-contact voltmeter probe and associated circuitry, for example. In certain embodiments, voltage changes or fluctuations corresponding to mil-sized subsurface defects may be measured. Although the time required for evaluating and testing a surface area using embodiments of the ES-NDET systems and methods may be longer in certain cases than that required using thermographic techniques, the likelihood of residual damage to the surface area is significantly reduced. Applications for the ES-NDET systems and methods may include, for example, testing and evaluation of surface coatings on satellite and aircraft components and other hardware to detect subsurface defects prior to deployment and detecting delaminations in composite materials. The systems and methods may also be used to study and evaluate the effects of Hall current (e.g., plasma) thrusters on spacecraft surfaces.

Electrical Properties of a Separated Coating in a Charging Environment

FIGS. 1A and 1B illustrate an article 100 comprising a dielectric surface coating 102 disposed over a conductive substrate 104. The coating 102 may be, for example, a thermal control paint, and the conductive substrate 104 may be a metallic film forming an exterior surface of a spacecraft. An area of the coating 102 may become separated from the substrate 104 due to, for example, a blister 106 formed in the coating 102 (FIG. 1A), or a void 108 or other defect formed in the substrate 104 (FIG. 1B). In other words, and area of the coating 102 and the substrate 104 may delaminate. The blister 106 in FIG. 1A and the void 108 in FIG. 1B are examples of subsurface defects. When the article 100 is exposed to a charging environment (e.g., a charging environment generated using, for example, any of: an electron gun, an ionizer, a gas blown over the article, a powder sprayed on the article, the triboelectric effect, or any other suitable charge source or charging method), the surface voltage on the area of separated coating will differ from the surface voltage on an adjacent defect-free surface area 112 of the coating 102. This voltage differential occurs because electrons on the defect-free surface area 112 are discharged to ground more directly than electrons on the area of the separated coating. FIGS. 1A and 1B illustrate different discharge paths that are possible. Electrons on the defect-free surface area 112 can migrate directly to ground via the underlying substrate 104, whereas electrons on the area of separated coating must first migrate (more or less laterally) off of the separated coating before reaching the defect-free surface area 112 and migrating to ground, and in the process of doing this they produce a voltage gradient within the separated dielectric coating.

In the area of separated coating (e.g., in the area of the coating 102 forming a blister 106 or the area of the coating 102 above a void 108), current resulting from the migration of charge towards the defect-free surface area 112 produces a voltage gradient along the separated coating due to electrical current flowing through the bulk resistivity of the coating material. The voltage gradient will be proportional to the current flow in the separated coating. Additionally, the charging current (from above in FIGS. 2 and 4) accumulates as it flows (laterally) through the dielectric towards the edges of the separated coating, resulting in a current gradient in the current flowing in the separated coating towards the defect-free surface area 112. There is an additional contribution to the current gradient that is proportional to the voltage at any point. In the defect-free surface area 112, on the other hand, the current simply flows directly through the coating 102 to the substrate 104, without any need to first migrate off of the area of separated coating.

The magnitude of the voltage gradient produced in this manner will be a function of a number of variables, including, for example, the thickness and material properties (e.g., bulk resistivity) of the coating 102, the area or size of the separated coating, the charging current density and the energy of the associated electrons. Additionally, a measured value of the voltage gradient may depend to an extent on characteristics of the particular voltage measurement device used. For example, when the voltage measurement device comprises a non-contact voltmeter probe, the voltage gradient measurement may depend on the geometry of the probe's sensing surface (e.g., round, square) and its area (e.g., a fraction of a square centimeter to several square centimeters).

Defect Modeling

FIG. 2 illustrates the geometry and boundary conditions for an area of separated coating, such as a blister 106, and comprises a rectangular dielectric film 114 of constant thickness d and length L that is grounded along its entire width W at opposite ends. In other words, the two ends are assumed to be connected to a defect-free surface area of the coating (such as defect-free surface area 112), whereas the sides along the lengths L are assumed to be unconnected to the defect-free surface area. Although the particular geometry and grounding configuration of the film 114 is chosen for purposes of conceptual simplicity and clarity, it will be appreciated that the following analysis may be extended to other geometries and configurations. It is assumed that the film 114 is in a charging environment with an incident electron current density of J (amps/cm$^2$), and that the energy of the electrons is such that the electrons penetrate[1] the film 114 to a depth t (cm) that is less than the film thickness (e.g., t<d). For this geometry and configuration, the voltage $V_{Blister}$ at a point $0 \leq x \leq L$ on the film 114 is given by:

$$V_{Blister}(x) = \frac{(\rho J/t)}{(K_B)^2}\left(1 - \frac{\cosh\left[K_B\left(x - \frac{L}{2}\right)\right]}{\cosh\left[K_B \frac{L}{2}\right]}\right), \quad (1)$$

where $$(K_B)^2 = \frac{(\rho J/t)}{(kT/q)},$$

and where $\rho$ is the bulk resistivity ($\Omega \cdot$cm), k is Boltzmann's constant (J deg$^{-1}$), T is the plasma temperature (deg Kelvin), q is the charge on an electron (coulombs), $\rho/t$ is the surface resistivity ($\Omega$/square), and kT/q (volts) is the plasma potential. At any value of x the voltage is assumed to be constant with respect to y ($0 \leq y \leq W$). The quantity $1/K_B$ is referred to as the sweep range, $L_B$ (cm). The sweep range[2] is the characteristic surface charge dissipation/diffusion length: it is the analog of the Debye length in plasma physics.[3] The peak voltage at the midpoint $$\frac{L}{2}$$

of the film 114 is given by:

$$V_{Blister}\left(\frac{L}{2}\right) = \frac{(\rho J/t)}{K_B^2}\left(1 - \frac{1}{\cosh\left[K_B \frac{L}{2}\right]}\right) \quad (2)$$

$$= (kT/q)\left(1 - \frac{1}{\cosh\left[K_B \frac{L}{2}\right]}\right).$$

The average voltage over the film 114 is given by:

$$\langle V_{Blister} \rangle = \left(\frac{kT}{q}\right)\left(1 - \frac{\tanh\left[K_B \frac{L}{2}\right]}{K_B \frac{L}{2}}\right). \quad (3)$$

[1] Electron penetration depth is a function primarily of electron energy and material density, and to a much lesser extent, of material composition. A penetration depth of 0.2 mils or so can be achieved, for example, with 20 KeV electrons and a material density of about 1.4 g/cm$^3$, or with 30 KeV electrons and a material density of about 3 g/cm$^3$. Many dielectric materials have densities in the 1-4 g/cm$^3$ range. Electron penetration depth vs. electron energy data for a wide variety of materials are available from, for example, the National Institute of Standards and Technology ESTAR Database (http://physics.nist.gov/PhysRefData/Star/Text/ESTAR.html).

[2] Following the standard practice in which decay constants are defined in terms of some characteristic quantity dropping to 1/e of its initial value, the sweep range corresponds to the distance over which the horizontal electric field drops to 1/e of its initial value. In the above example, in the limit where $$K_B \frac{L}{2} \gg 1,$$

it may be shown that the corresponding ratio of electric field strengths becomes $$\left|\frac{E(L_B)}{E(0)}\right| \to |(\text{Sinh}[1] - \text{Cosh}[1])| = e^{-1}.$$

[3] In plasma physics, the Debye length is the scale over which mobile charge carriers (e.g., electrons) screen out electric fields in plasmas and other conductors. In other words, the Debye length is the distance over which significant charge separation can occur.

For nonconductive dielectric materials where the sweep range $L_B$ is much less than the film 114 size (e.g., where $$K_B \frac{L}{2} \gg 1),$$

the peak voltage given by equation (2) can become substantial and in the limit reach a level equal to the ambient plasma potential, $$V_{Blister}\left(\frac{L}{2}\right) \to (kT/q), \tag{4}$$

almost everywhere except near the boundaries at x=0 and x=L, where it drops rapidly to zero. The average voltage given by equation (3) then becomes:

$$\langle V_{Blister}\rangle = \frac{kT}{q}\left(1 - \frac{1}{K_B \frac{L}{2}}\right). \tag{5}$$

For conductive dielectric materials where the sweep range $L_B$ is much greater than the film 114 size (e.g., where $$K_B \frac{L}{2} \ll 1),$$

the peak voltage given by equation (2) will be limited by this ratio of the length of the area of separated coating to sweep range, yielding:

$$V_{Blister}\left(\frac{L}{2}\right) \to \frac{1}{2}(kT/q)\left(\frac{K_B L}{2}\right)^2 = (kT/q)\frac{(K_B L)^2}{8}. \tag{6}$$

Figure 3:
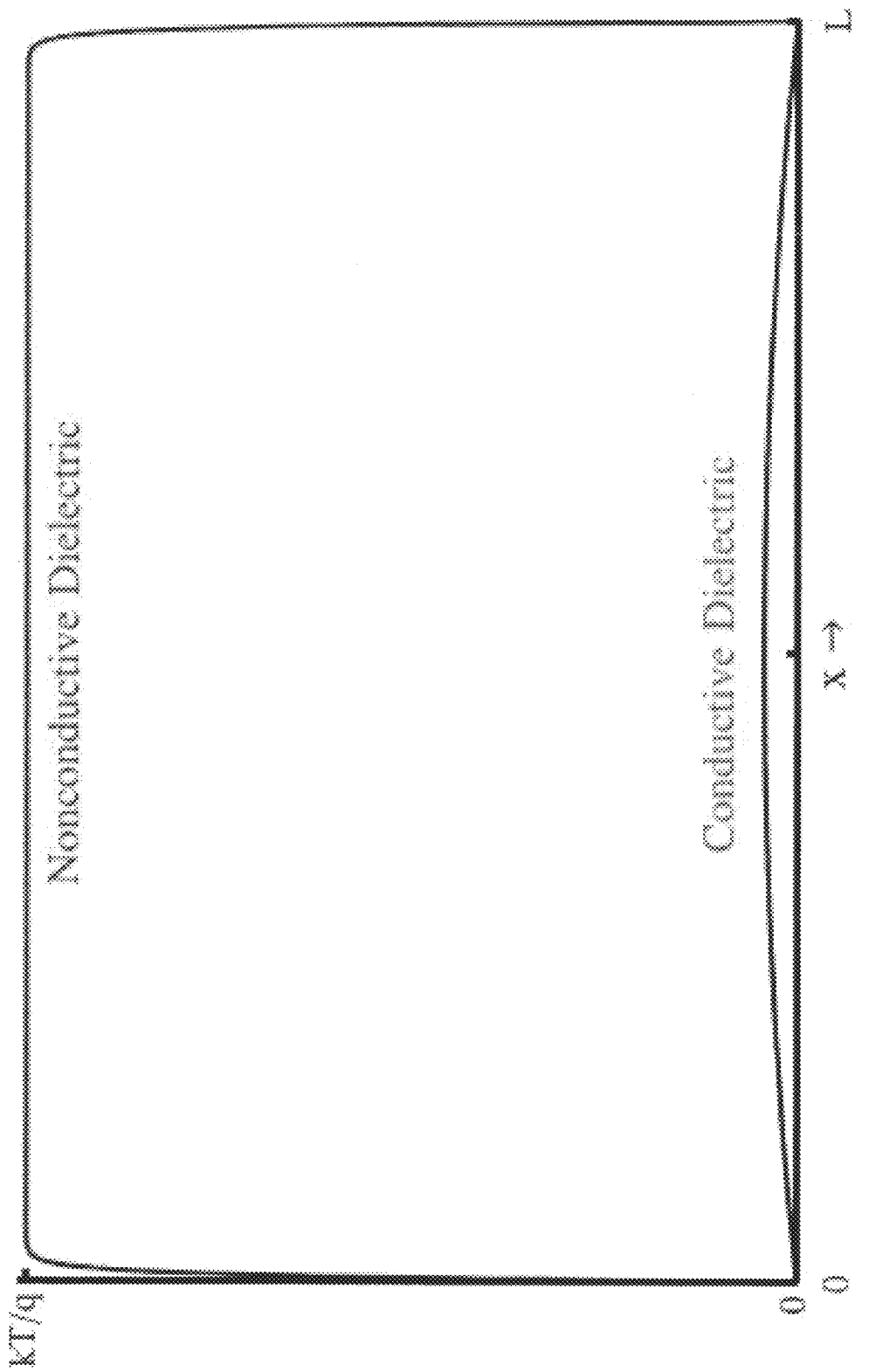
FIG. 3 illustrates examples of voltage profiles of nonconductive and conductive dielectric films.

Examples of voltage profiles for nonconductive and conductive dielectric films 114 are illustrated in FIG. 3.

Referring again to equation (1), consider the case of a conductive dielectric where the sweep range $L_B$ is much greater than the film 114 size, e.g., $$K_B \frac{L}{2} \ll 1.$$

In this case, because $$K_B \frac{x}{2} < K_B \frac{L}{2} \ll 1,$$

the voltage $V_{Blister}$ on the film 114 given by equation (1) reduces to:

$$V_{Blister}(x) = \frac{1}{2}\frac{\rho J}{t} \cdot x \cdot (L-x). \tag{7}$$

The peak voltage at the center of the film 114 (e.g., at $$x = \frac{L}{2}$$

is given by:

$$V_{Blister}\left(\frac{L}{2}\right) \approx \frac{1}{8}\frac{\rho J}{t}L^2. \tag{8}$$

The average voltage over the entire film 114, on the other hand, is given by:

$$\langle V_{Blister}\rangle = \frac{1}{12}\frac{\rho J}{t}L^2. \tag{9}$$

Equation (7) is an expression of the voltage at any point $0 \leq x \leq L$ on a rectangular surface that is grounded at opposite ends along its entire width, W. This may be shown by deriving equation (7) for the case of a conductive dielectric by means of Ohm's Law as follows.

Figure 4:
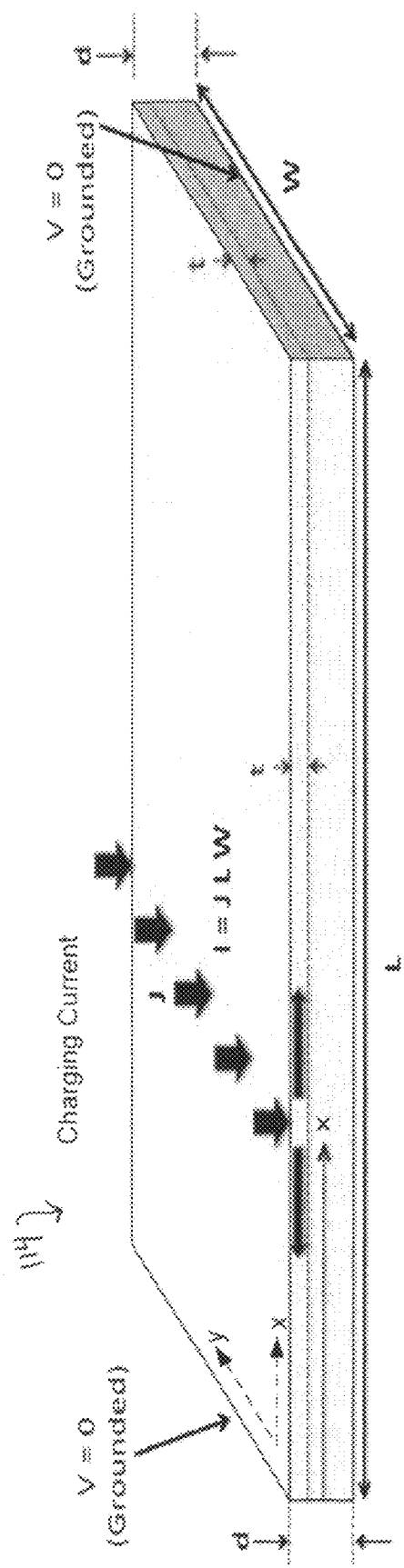

Assume that a charging current of density J is normally incident over the entire surface of the rectangular dielectric film 114. The total incident current is I=J×Area=J×(L×W). As shown in FIG. 4, a part of the charging current goes to the grounded length W on the left, with the remainder flowing towards the grounded length W on the right. The incident current will penetrate the surface of the film 114 to a depth t, the electron penetration depth. The electrical resistance that this current encounters in flowing to the left and to the right, through distances x and L−x, respectively, and a cross-sectional area t×W, will be given by:

$$R_{Left} = \frac{1}{2}\left(\frac{\rho}{tW}\right)x \tag{10a}$$

and $$R_{Right} = \frac{1}{2}\left(\frac{\rho}{tW}\right)(L-x). \tag{10b}$$

The distributed resistance in the two parallel paths to the grounded lengths W at x=0 and x=L then becomes:

$$R_{Blister} = R_{Left} \| R_{Right} = \frac{R_{Left}\cdot R_{Right}}{R_{Left}+R_{Right}} = \frac{1}{2}\left(\frac{\rho}{tW}\right)\frac{x\cdot(L-x)}{L}. \tag{11}$$

According to Ohm's Law, the voltage at any point between the grounded lengths L is:

$$V_{Blister}(x) = I \cdot R_{Blister} = (JLW)\cdot\frac{1}{2}\cdot\left(\frac{\rho}{tW}\right)\cdot\left(\frac{x\cdot(L-x)}{x}\right), \tag{12}$$

which reduces to:

$$V_{Blister}(x) = \frac{1}{2}\frac{\rho J}{t}\cdot x\cdot(L-x). \tag{13}$$

Equation (13) and equation (7) are identical. A similar derivation can be made in the case of a nonconductive dielectric. This case is more analytically complex because it is only near the endpoints (x=0 and x=L) that the voltage differs appreciably from kT/q. Thus, it is only near these endpoints that there is any appreciable electric field, or any appreciable current, as shown in FIG. 3.

Modeling Defect-Free Surfaces

Figure 5:
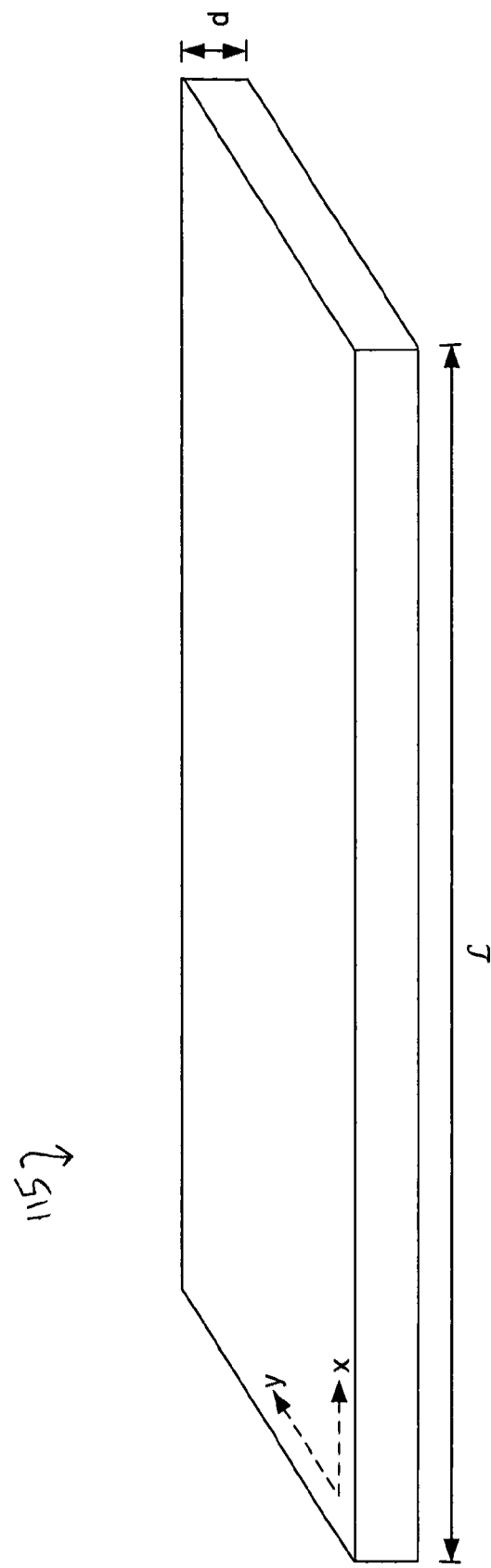
FIG. 5 illustrates the geometry of a defect-free area of a dielectric coating according to one embodiment.

FIG. 5 illustrates the geometry of a defect-free surface area of a coating, such as a defect-free surface area 112, and comprises a rectangular dielectric film 115 of constant thickness d and length $\mathcal{L}$. The surface voltage on the film 115 is given by:

$$V_{Flat}(x) = (\rho J d)\left(1 - \frac{\cosh\left[\frac{1}{\sqrt{td}}\left(x - \frac{\mathcal{L}}{2}\right)\right]}{\cosh\left[\frac{1}{\sqrt{td}}\frac{\mathcal{L}}{2}\right]}\right). \tag{14}$$

Since $$\frac{1}{\sqrt{td}}\frac{\mathcal{L}}{2} \gg 1$$

for most dielectric coatings, the voltage will be constant over almost the entire film 115, except for two very narrow regions at either end:

$$V_{Flat}(x) = \rho J d. \tag{15}$$

It will be appreciated that this is a voltage drop through a dielectric coating of thickness, d.

Detectability of Defects

Figure 6:
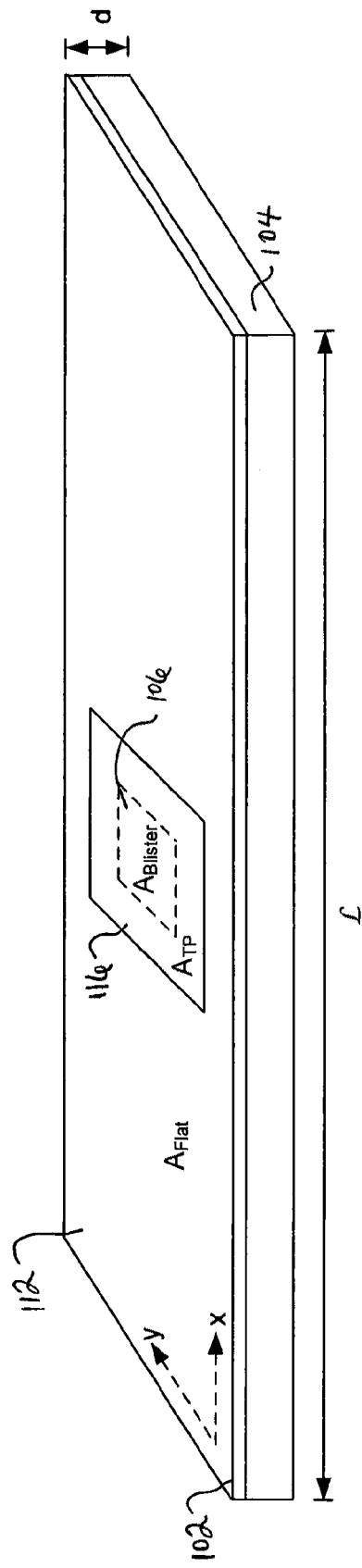
FIG. 6 illustrates a sensing surface of a voltage measurement device positioned to measure voltage on a dielectric-coated conductive substrate comprising an area of separated coating and a defect-free surface area.

FIG. 6 illustrates a sensing surface 116 of a voltage measurement device positioned to measure voltage on a dielectric-coated conductive substrate comprising an area of separated coating (e.g., a blister 106) and a defect-free surface area 112. The dielectric-coated conductive substrate may be identical to that shown in FIG. 1A or 1B, for example. The area of the sensing surface 116, the area of separated coating and the defect-free surface area 112 are indicated by $A_{TP}$, $A_{Blister}$, $A_{Flat}$, respectively. Subsurface defects, such as a blister 106, can be detected when the difference between the measured voltage on the area containing the separated coating and the measured voltage on the defect-free surface area 112 is sufficiently greater than the noise floor of the voltage measurement device. The voltage measurement device may comprise, for example, a non-contact voltmeter probe (such as a non-contact voltmeter probe available from Trek, Inc. of Medina, N.Y.) having a noise floor that is low relative to the measured voltage difference. In certain embodiments, the actual voltage indicated by the voltage measurement device, $V_{TP}$, may be the weighted average of the voltages averaged over the relevant surface areas, e.g., $$V_{TP} = \frac{A_{Blister}\langle V_{Blister}\rangle + (A_{TP} - A_{Blister})V_{Flat}}{A_{TP}}, \tag{16}$$

where $\langle V_{Blister}\rangle$ is the average voltage on the area containing a separated coating and $V_{Flat}$ is the voltage on the defect-free surface area 112. The difference or change between voltage measurements on the area containing a separated coating and the defect-free surface area 112 will therefore be:

$$\Delta V = V_{TP} - V_{Flat} = \frac{A_{Blister}}{A_{TP}} \cdot (\langle V_{Blister}\rangle - V_{Flat}). \tag{17}$$

Example of ΔV Calculation

An example of the calculation of the voltage difference ΔV of equation (17) is as follows. Assume parameter values as follows:

$$kT/q = 20 \text{ kVolts } t = 0.2 \text{ mils} = 5 \times 10^{-4} \text{ cm}$$

$$J = 10 \text{ nA/cm}^2 \ d = 10 \text{ mils} = 25.4 \times 10^{-3} \text{ cm}$$

$$\rho = 1 \times 10^{11} \Omega \cdot \text{cm } L = 20 \text{ mils} = 5 \times 10^{-2} \text{ cm}$$

Then:

$$V_{Flat} = \rho J d = 25.4 \text{ Volts}. \tag{18}$$

Since the sweep range $L_B$ extends beyond the assumed size of the length, L of the area of separated coating, e.g., $$L_B = \sqrt{\frac{kT/q}{\rho J/t}} = 0.1 \text{cm} > 0.05 \text{cm}, \tag{19}$$

equation (8) may used to calculate the peak voltage on the area containing a separated coating as follows:

$$V_{Blister}(L/2) = \frac{1}{8}\frac{\rho J}{t}L^2 = 625 \text{ Volts}, \tag{20}$$

and equation (9) may be used to calculate the average voltage on the area containing a separated coating as follows:

$$\langle V_{Blister}\rangle = \frac{1}{12}\frac{\rho J}{t}L^2 = 417 \text{ Volts}. \tag{21}$$

Assuming an $A_{TP}$ value of 1 cm², for the example above ΔV is calculated to be:

$$\Delta V = \frac{(0.05)^2}{1} \cdot (417 \ V - 25 \ V) = 0.98 \text{ Volts}. \tag{22}$$

In cases where the noise floor of the voltage measurement instrument is small relative to ΔV (e.g., a noise floor of approximately 4 mV for the above example), it will be appreciated that the difference or change between voltage measurements on the area containing a separated coating and the defect-free surface area 112 can be used to detect the subsurface defect.

In order to avoid the possibility of causing residual damage, the dielectric surface coating 102 should not be stressed beyond its breakdown strength. The magnitude of the electric field is just the magnitude of voltage gradient on the area containing the separated coating, and in the example above, the maximum horizontal induced electric field at either end of the area separated coating is given by:

$$\|E_{Hor}(x=0, L)\| = \left|\frac{\rho J}{2t}(L - 2x)\right|_{x=0} = \frac{\rho J}{2t}L = 127 \text{ Volts/mil}. \tag{23}$$

In the vertical direction, the maximum field strength equals the maximum difference between the voltages of the area containing the separated coating and the defect-free surface area 112, divided by the film thickness, d:

$$E_{Vert} = \frac{625 \text{ Volts}}{10 \text{ mils}} = 62.5 \text{ Volts/mil}. \tag{24}$$

For many dielectric materials, the typical breakdown strength for thick films is on the order of several hundred volts/mil; for thin films (e.g., with thicknesses approximately 1-10 mils) the dielectric strength is in the order of several thousand volts/ mil. This happens because trapped charges on a thin insulator do not accumulate due to the proximity of the substrate and hence can drain off the surface easily. A stronger electric field is therefore needed to induce an electron avalanche.[4]

[4] For most dielectrics the breakdown strength obeys the following inverse square-root relationship:

$$E_{BD_2} = E_{BD_1} \sqrt{\frac{d_1}{d_2}},$$

e.g., thinner materials have a greater breakdown strength than do thicker materials.

Figure 7:
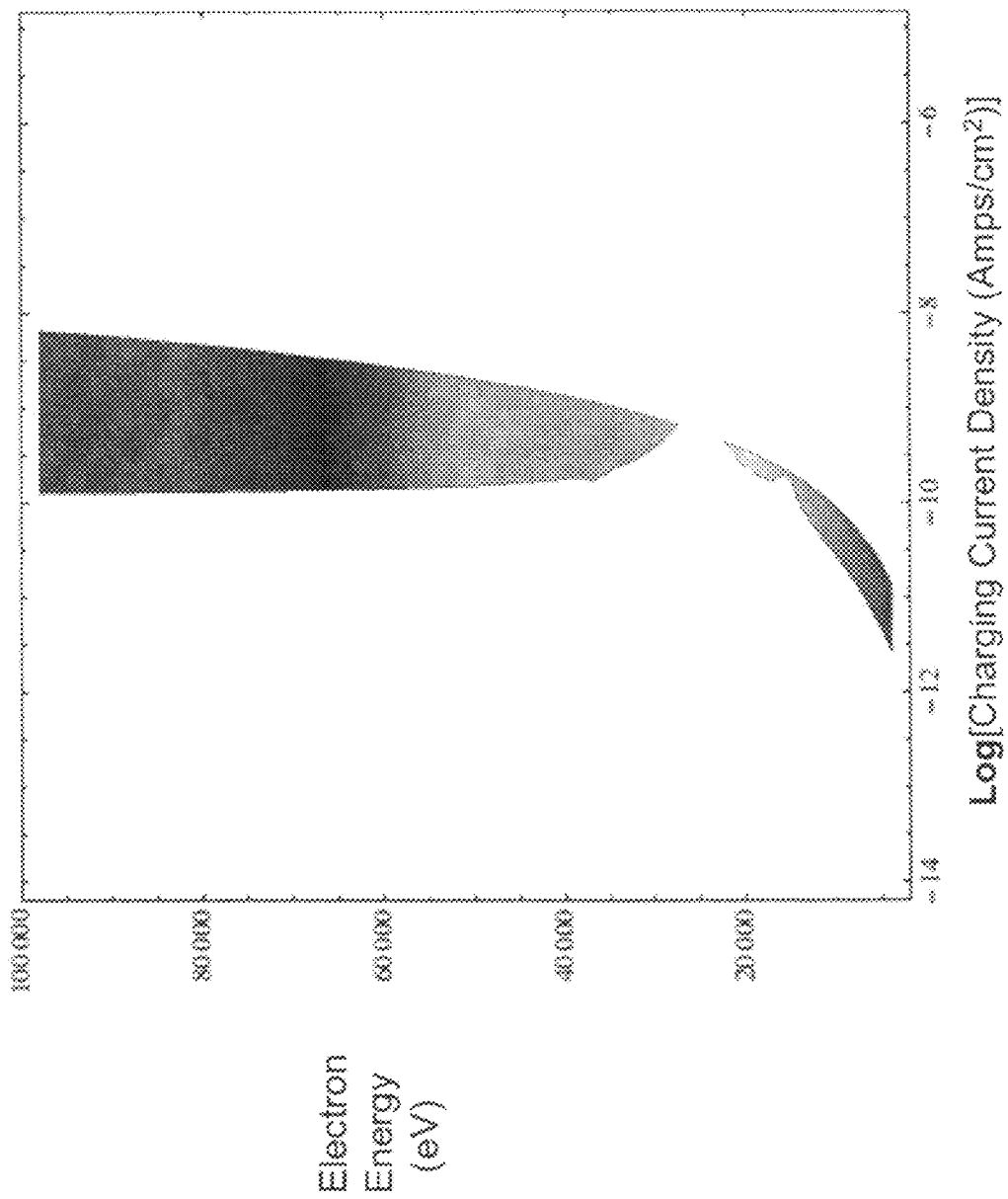
FIG. 7 is a plot of non-damaging combinations of the charging current density and electron energy according to one embodiment.

The charging environment may be controlled to minimize or reduce the likelihood of damaging the dielectric surface coating 102. This control may be performed directly or indirectly, depending on the type of charge source used to create the charging environment. In embodiments in which the charge source comprise an electron gun, for example, a "region-of-operation" plot (FIG. 7) may define charging current density and electron energy combinations for inducing electric fields that can be withstood by the coating 102. The region-of-operation plot for a particular coating 102 may be determined, for example, by determining, for each of a number of possible charging current density and electron energy combinations, an amount of current that will be deposited in the coating 102, the resulting distribution of the current in different regions of the coating 102 and the resulting electric field in the coating 102. These determinations may depend to an extent on physical properties (e.g., area, size, thickness, bulk resistivity) of the dielectric material and can be performed using processor-based simulations, for example. To define the region-of-operation plot, the resulting electric fields may be compared to a known breakdown field for the particular coating 102 to determine which of the possible combinations of charging current density and electron energy will not damage the coating 102. The charging environment may then be directly controlled in accordance with the non-damaging combinations of charging current density and electron energy.

In other embodiments, direct control of the charging environment may not be practical or possible. Such may be the case, for example, in embodiments in which the charging environment is generated using the triboelectric effect, or other charging mechanism for which the amount of transferred charge cannot be directly or easily determined. In such cases, it may be necessary to determine a priori (e.g., through experimentation) one or more operating parameters of the charge source (e.g., the type and/or amount of material used to produce triboelectrification, the type of contact/motion used to produce triboelectrification, the type of powder or gas used to generate charge, the flow rate and/or speed of the powder or gas, humidity and/or temperature of the charging environment) and the dependency of the charging environment on the one or more operating parameters. In this way, the charging environment may be calibrated and indirectly controlled based on the one or more operating parameters.

Non-Rectangular Geometries

Although the discussion above assumes rectangular coating separation geometries, a similar analysis of other geometries is also possible, albeit more mathematically complex. For example, the voltage at some distance from the center, r, on a circular area of separated coating of radius R is given by:

$$V_{Blister}(r) = \frac{kT}{q} \left(1 - \frac{I_0\left(r\sqrt{\frac{\rho J/t}{kT/q}}\right)}{I_0\left(R\sqrt{\frac{\rho J/t}{kT/q}}\right)}\right), \quad (25)$$

where $I_0(x)$ is the modified Bessel function of the first kind. The voltage averaged over the entire circular area of separated coating is given by:

$$\langle V_{Blister}\rangle = \frac{kT}{q}\left(1 - \frac{{}_0\tilde{F}_1\left(;2;\frac{R^2}{4}\frac{\rho J/t}{kT/q}\right)}{I_0\left(R\sqrt{\frac{\rho J/t}{kT/q}}\right)}\right), \quad (26)$$

where ${}_p\tilde{F}_q(a_1, \ldots, a_p; b_1, \ldots, b_q; z)$ is the regularized hypergeometric function.

In order to facilitate comparison with the case of a rectangular area of separated coating, the diameter (2R) of the circular area of separated coating is chosen to be the same as the length L in the rectangular example. All of the other parameters remain the same:

$kT/q$=20 kVolts $t$=0.2 mils=5×10$^{-4}$ cm $J$=10 nA/cm$^2$ $d$=10 mils=25.4×10$^{-3}$ cm $\rho$=1×10$^{11}$ Ω·cm $R$=10 mils=2.5×10$^{-2}$ cm In this case we find:

$\Delta V$=0.45 Volts, (27)

$E_H$=71 Volts/mil, (28)

and $$E_{Vert} = \frac{180}{10} = 18 \text{ Volts/mil}. \quad (29)$$

These values are on the order of one half of the corresponding values for the rectangular case, and this difference is presumably due to the difference in geometries and grounding configurations between the two cases. Again, the ΔV is well above noise floor of available voltage measurement devices (e.g., approximately 4 mV or less for non-contact voltmeter probes), and the maximum electric field is well below typical breakdown strengths for dielectric materials.

Figure 8:
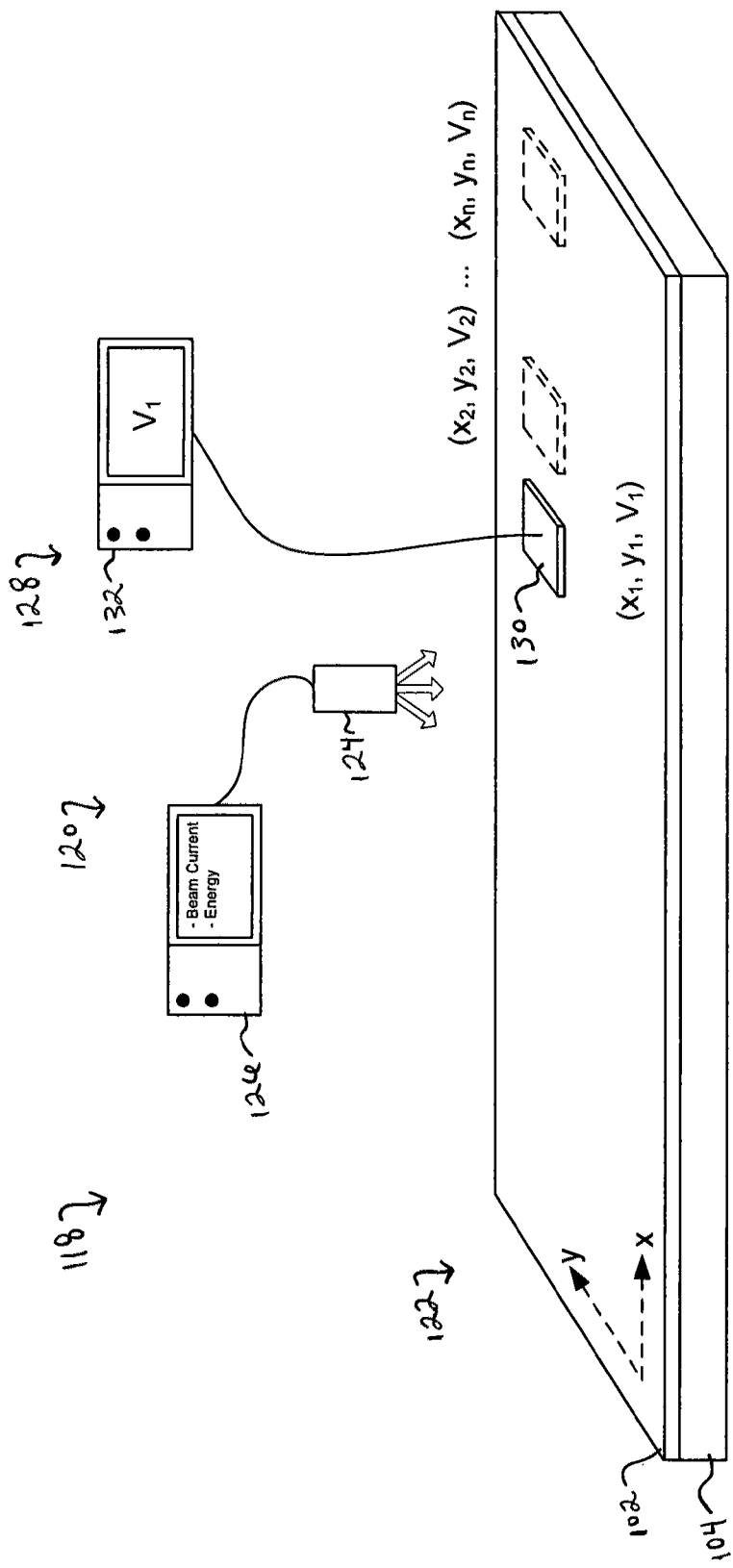
FIGS. 8, 10, 12 and 13 illustrate defect detection systems according to various embodiments.

FIG. 8 illustrates an ES-NDET system 118 according to one embodiment. The system 118 may comprise a charge source 120 for generating a charging environment to produce a current (e.g., a steady-state or quasi steady-state current) on a surface area of an article 122 to be evaluated and tested for subsurface defects. The article 122 may be similar to the article 100 of FIGS. 1A and 1B, for example, and comprise a dielectric surface coating 102 disposed over a conductive substrate 104. In one embodiment, the charge source 120 may comprise an electron gun 124 and a power supply 126 coupled to the electron gun 124 for outputting an electron beam having a desired current and energy. The power supply 126 may permit independent adjustment of the electron beam current and energy. In certain embodiments, these adjustments may be performed manually at the power supply 126. In other embodiments, these adjustments may be performed remotely by a computer system or other processor-based device (e.g., computer system 160 of FIG. 14 discussed below) in communication with the power supply 126 via, for example, an RS-422/RS-485 serial interface.

It will be appreciated that the electron gun 124 is but one example of a charge source 120, and that other suitable charge sources (e.g., an ionizer, a gas blown over the article, a powder sprayed on the article, the triboelectric effect) may alternatively be used. It will further be appreciated that, depending on the type of charge source 120 used, generation of the charging environment by the charge source 120 may additionally or alternatively comprise producing a voltage profile (e.g., a steady-state or quasi steady-state voltage profile) on the surface area of the article 122.

The system 118 may comprise a voltage measurement device 128 for measuring voltages on the surface area of the article 122 and, optionally, for providing a visual indication of the measured voltages. In one embodiment, the voltage measurement device 128 may include an electrostatic voltmeter comprising a non-contact voltmeter probe 130 coupled to a voltmeter circuit 132. The non-contact voltmeter probe 130 may comprise, for example, a Model 6000B-8 non-contact voltmeter probe, and the voltmeter circuit 132 may comprise, for example, a Model 344 electrostatic voltmeter, both available from Trek, Inc. In certain embodiments, voltage measurements of the voltage measurement device 128 may be monitored and/or controlled by a computer system or other processor-based device (e.g., computer system 160 of FIG. 14 discussed below) in communication with the voltage measurement device 128 via a communication link, such as, for example, an analog communication link and/or an RS-232 serial interface.

Figure 9:
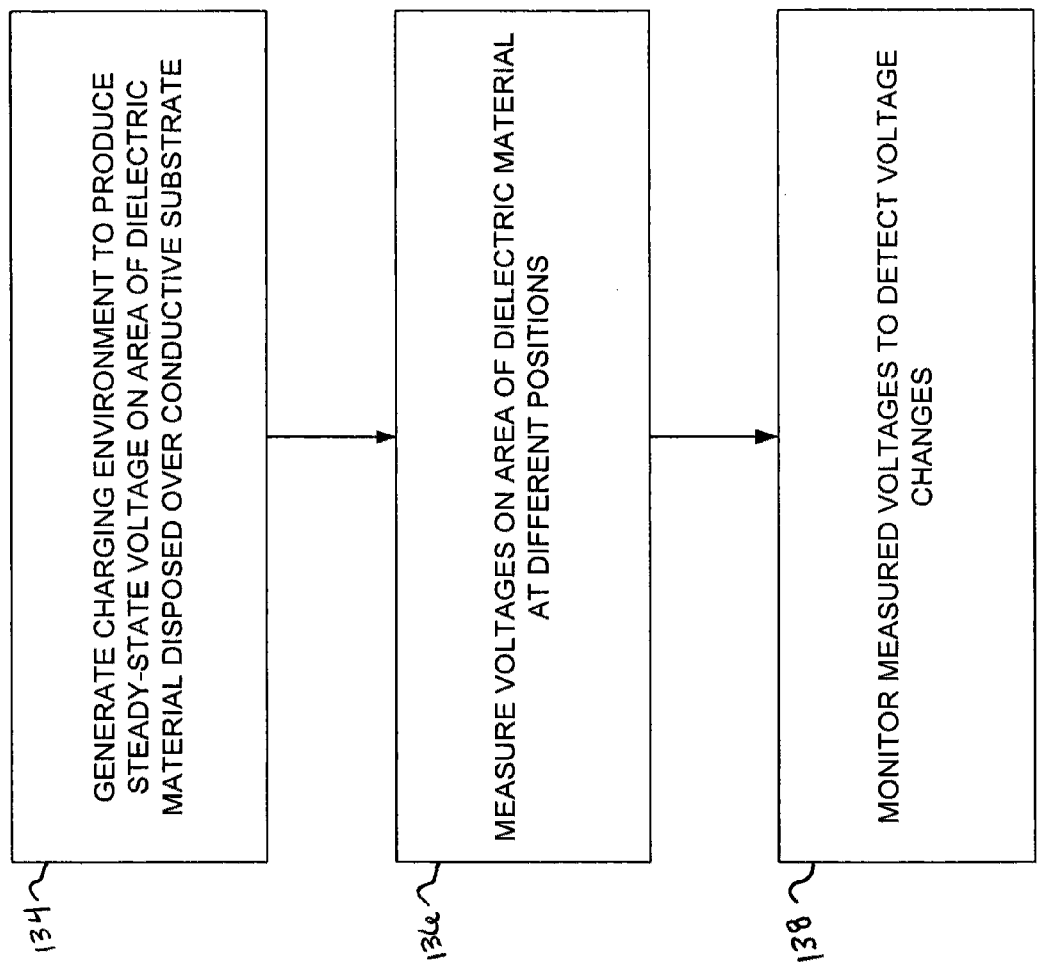
FIG. 9 is a process according to one embodiment.

FIG. 9 illustrates one embodiment of a process implemented by the system 118. At step 134, the charge source 120 is activated and controlled to generate a charging environment to produce a current (e.g., a steady-state or quasi steady-state current) on the surface area of the article 122. In embodiments in which the charge source 120 comprises an electron gun 124 and a power supply 126, for example, the electron beam current and energy may be controlled (either manually or automatically by a processor-based device) in accordance with a region-of-operation plot (FIG. 7) specific to the coating 102 of the article 122. It will be appreciated that charge sources other than an electron gun 124 (e.g., an ionizer, a gas blown over the article, a powder sprayed on the article, the triboelectric effect) may alternatively be used.

At step 136, voltages at a plurality of positions or locations on the surface area of the article 122 are measured using the voltage measurement device 128. In embodiments in which the voltage measurement device 128 comprises a non-contact voltmeter probe 130, the measurements may be performed, for example, by continuously scanning the probe 130 over the surface area of the article 122 and simultaneously measuring the voltage at a plurality of positions throughout the scanning process (e.g., $(x_1, y_1, V_1), (x_2, y_2, V_2) \ldots (x_n, y_n, V_n)$).

At step 138, the measured voltages are analyzed during the scanning process (or after the scanning and measurement process is completed) to detect changes or fluctuations in voltage that occur between two measurements, or over a range of measurements. As will be appreciated from the discussion above in connection with FIG. 6, such changes or fluctuations may be used to indicate the presence of subsurface defects (e.g., a blister 106 or a void 108) in the article 122 at positions or locations corresponding to the changes or fluctuations.

Figure 10:
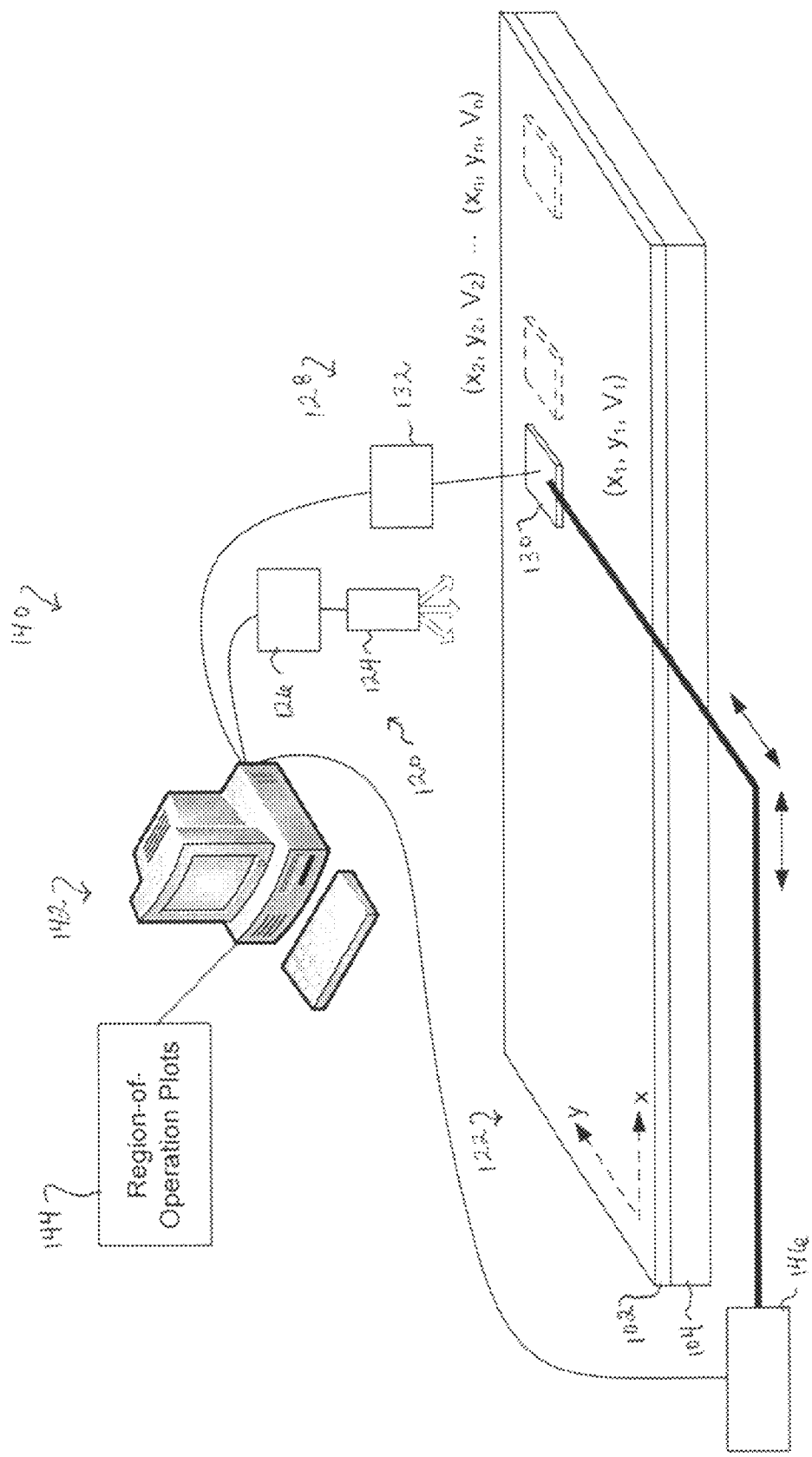

FIG. 10 illustrates another embodiment of an ES-NDET system 140 comprising a computer 142 or other processor-based device (e.g., computer system 160 of FIG. 14 discussed below) programmed to monitor and/or control operation of the charge source 120 and the voltage measurement device 128. The computer 142 may be in communication with a power supply 126 of a charge source 120 via, for example, an RS-422/RS-485 serial interface communication link, to control the beam current and energy output by an electron gun 124 coupled to the power supply 126. In one embodiment, the computer 142 may be programmed to receive user input describing physical properties (e.g., area, size, thickness, bulk resistivity) of the dielectric surface coating 102. Based on this information, the computer 142 may select an appropriate region-of-operation plot (FIG. 7) from a database 144 containing a number of region-of-operation plots for different coatings. The computer 142 may then control the power supply 126 in accordance with the selected region-of-operation plot to ensure that only non-damaging combinations of charging current density and electron energy are produced by the electron gun 124.

The system 140 may comprise one or more actuators 146 in communication with the computer 142 for controlling and varying a position or location of the voltage measurement device 128. For example, in embodiments in which the voltage measurement device 128 comprises a non-contact voltmeter probe 130, each actuator 146 may be mechanically coupled to the probe 130 to control and vary the position of the probe 130 over the surface area of the article 122 responsive to a positioning signal output by the computer 142. The positioning signal may define a measurement pattern of the probe 130 over the surface area of the article 122 and be generated by the computer 142 based on, for example, characteristics of the probe 130 (e.g., geometry and/or area or size of the probe sensing surface) and/or user inputs specifying a shape and size of the surface area of the article 122. Additionally, the positioning signal may be generated by the computer 142 to optimize the efficiency of the voltage measurement process by, for example, controlling the manner of probe 130 movement (e.g., continuous, discrete, oscillatory), the speed of the probe 130, and the path of the probe 130 over the surface area of the article 122 (e.g., linear, curved, zig-zag). It will be appreciated that certain of these positioning signal variables (e.g., continuous or discrete movement, probe speed) may be dictated to an extent by the response characteristics of the particular probe 130. In certain embodiments, the one or more actuators 146 may comprise a servomotor and associated control circuitry for controlling and positioning the probe 130 over the surface area of the article 122 with a suitable degree of accuracy. In certain embodiments, feedback regarding the position or location of the probe 130 may be transmitted from position sensors located in the one or more actuators 146 (or elsewhere) to the computer 142.

As shown in FIG. 10, the computer 142 may be in communication with the voltage measurement device 128 (e.g., probe 130) to receive its output as the position of the measurement device 128 over the surface area of the article 122 is controlled and varied (e.g., by the one or more actuators 146. In certain embodiments, the computer 142 may record voltage measurements received from the voltage measurement device 128 and the position of each measurement (e.g., based on positional feedback from the one or more actuators 146) in a substantially continuous manner, or at discrete intervals (e.g., corresponding to discrete positions of the probe 130). The voltage measurements may be analyzed by the computer 142 as they are recorded (or after all measurements are completed) to detect changes or fluctuations in voltage that occur between two measurements, or over a range of measurements. As will be appreciated from the discussion above in connection with FIG. 6, such changes or fluctuations may be used to indicate the presence of subsurface defects (e.g., a blister 106 or a void 108) in the article 122 at positions corresponding to the changes or fluctuations. In this way, the computer 142 may determine the presence of any subsurface defects in the article 122 and their corresponding positions. Additionally, based on the magnitude of any voltage change or fluctuation that is determined to be the result of a subsurface defect, and/or based on the number of measurements over which such a change or fluctuation occurs, the computer 142 may determine or estimate the size of the subsurface defect. This information may be output to a user by the computer 142, for example, in a graphical format (e.g., on a graphical representation of the article 122 generated by the computer 142), or in a text-based format.

Figure 11:
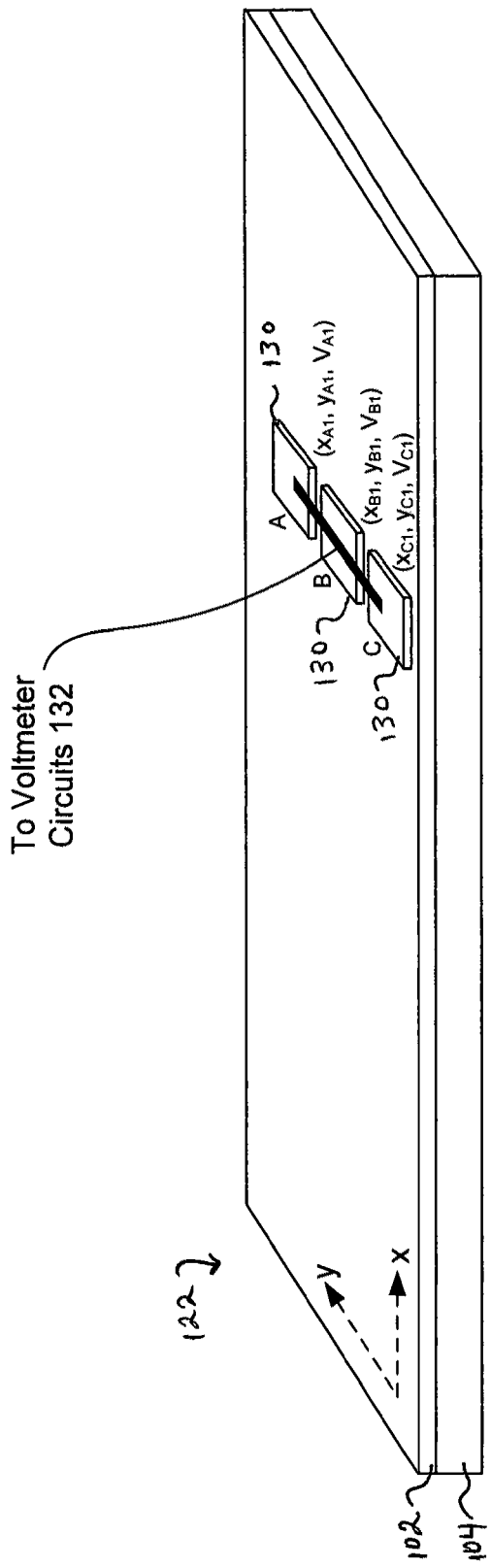
FIG. 11 illustrates a non-contact voltmeter probe configuration according to one embodiment.

In certain embodiments, more than one voltage measurement device 128 may be used simultaneously to increase the efficiency of measuring the voltage on the surface area of the article 122. As shown in FIG. 11, for example, two or more non-contact voltmeter probes 130 can be used simultaneously to increase the area of measurement, thereby reducing measurement time.

Figure 12:
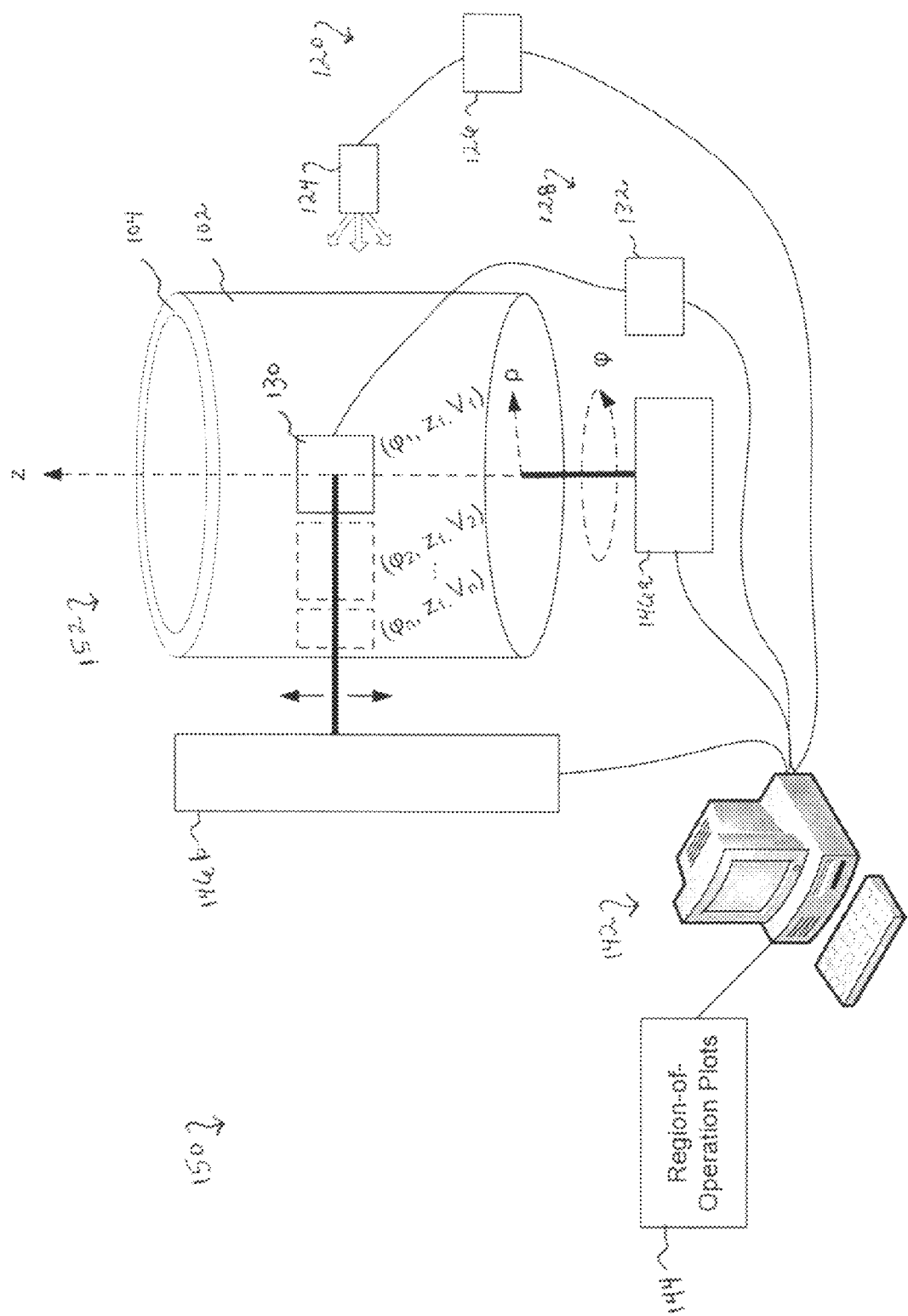

Although the embodiment of the system 140 is illustrated being used with an article 122 comprising a generally planar surface area, embodiments of the system 140 are not limited to such geometries. FIG. 12, for example, illustrates one embodiment of an ES-NDET system 150 that may be used to detect subsurface defects in an article 152 comprising a cylindrical geometry. In this embodiment, the one or more actuators 146 may include a first actuator 146a for rotating the article 152 (indicated angle φ) about an axis of symmetry (indicated by the z axis), and a second actuator 146b for changing a position of a voltage measurement device 128 (e.g., a non-contact voltmeter probe 130) along the direction of the axis of symmetry. Accordingly, based on positional feedback received from the actuators 146a, 146b (or other source) and voltage measurements recorded from the output of the voltage measurement device 128, the computer 142 may detect the presence of any subsurface defects in the article 122 and determine the position of each (e.g., using (φ, z) coordinate pairs).

Figure 13:
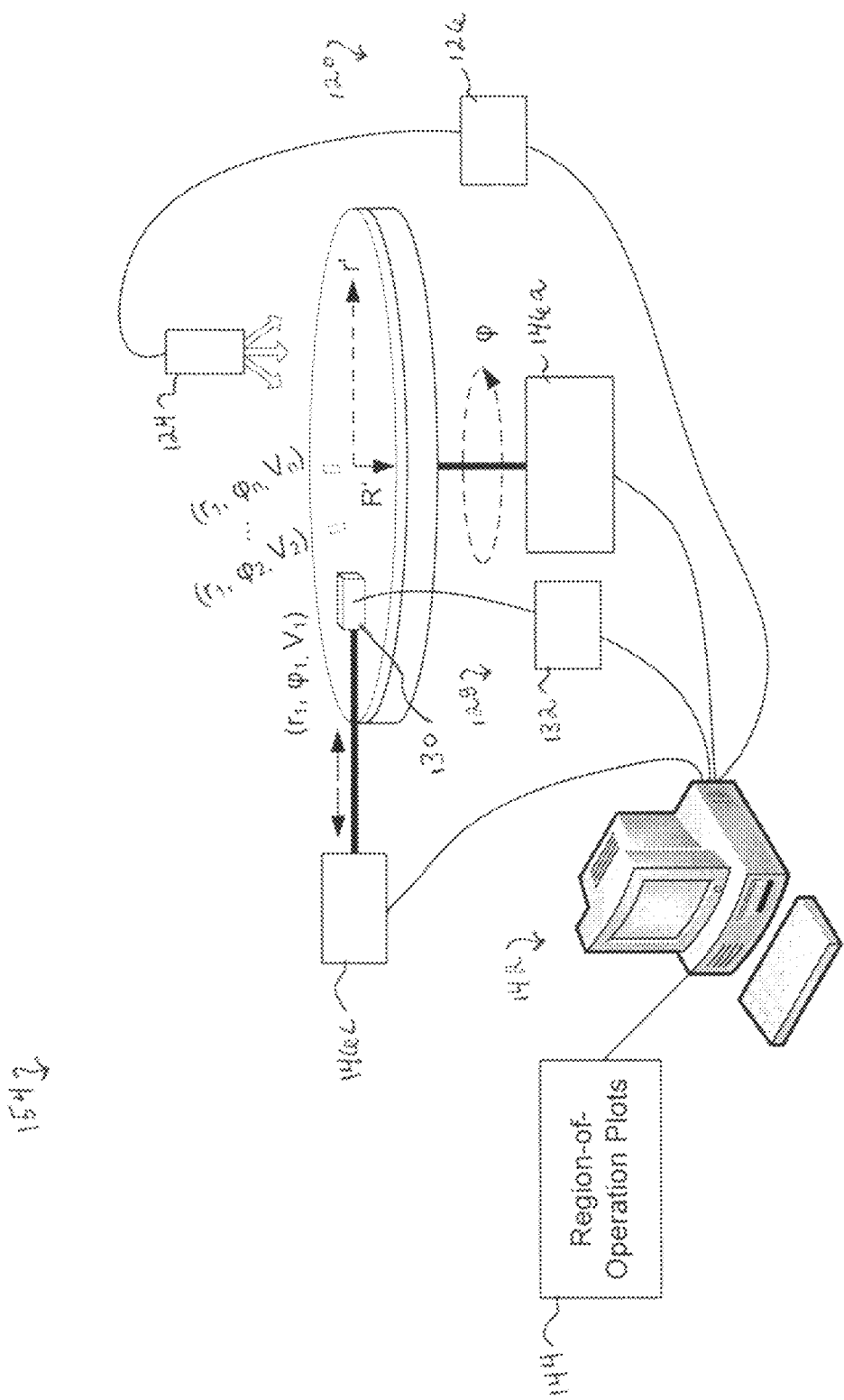

FIG. 13 illustrates an embodiment of an ES-NDET system 154 that may be used to detect subsurface defects in an article 156 comprising a disc-shaped geometry. In this embodiment, the one or more actuators 146 may include a first actuator 146a for rotating the article 152 (indicated by angle φ) about an axis of symmetry, and a second actuator 146c for controlling and varying a radial position (indicated by the r' axis) of a voltage measurement device 128 (e.g., a non-contact voltmeter probe 130) relative to the surface of the article 156. Accordingly, based on positional feedback received from the actuators 146a, 146c (or other source) and voltage measurements recorded from the output of the voltage measurement device 128, the computer 142 may detect the presence of any subsurface defects in the article 122 and determine the position of each (e.g., using (r', φ) coordinate pairs).

Figure 14:
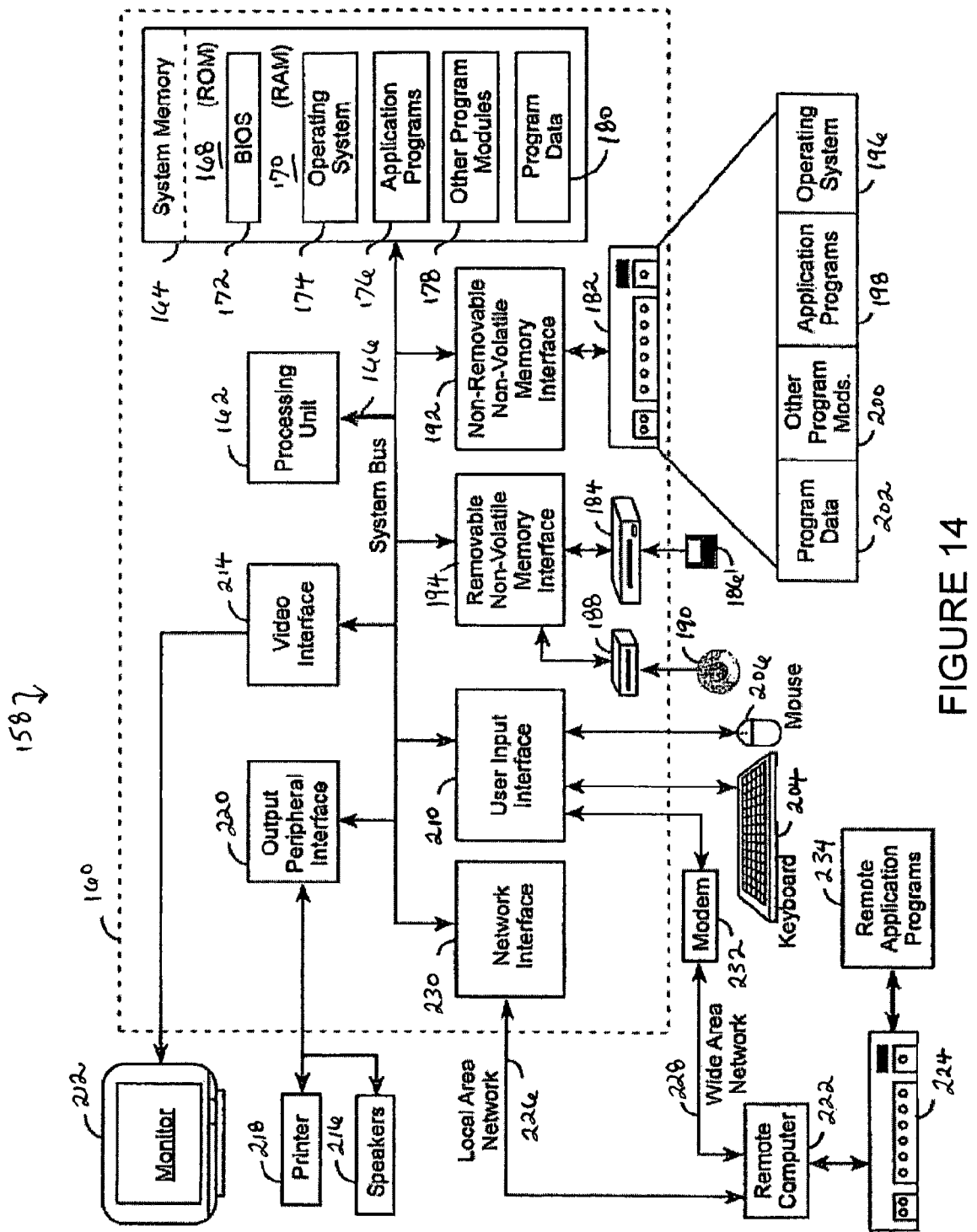
FIG. 14 illustrates a computing system environment according to one embodiment.

FIG. 14 and the following discussion are intended to provide a brief general description of a suitable computing environment 158 in which aspects of described embodiments of ES-NDET systems and methods may be implemented. It should be understood, however, that handheld, portable, and other computing devices and computing objects of all kinds are contemplated for use in connection with the described embodiments. The computing system environment 158 is only one example of a suitable computing environment and is not intended to suggest any limitation as to the scope of use or functionality of the described embodiments. Neither should the computing environment 158 be interpreted as having any dependency or requirement relating to any one or combination of components illustrated in the operating computing environment 158. With reference to FIG. 14, one embodiment of a system for implementing the described embodiments comprises a general purpose computing device in the form of a computer system 160. Components of the computer system 160 may comprise a processing unit 162, a system memory 164, and a system bus 166 that couples various system components including the system memory 164 to the processing unit 162. The system bus 166 may be any of several types of bus structures including a memory bus or memory controller, a peripheral bus, and a local bus using any of a variety of bus architectures. By way of example, and not limitation, such architectures include Industry Standard Architecture (ISA) bus, Micro Channel Architecture (MCA) bus, Enhanced ISA (EISA) bus, Video Electronics Standards Association (VESA) local bus, and Peripheral Component Interconnect (PCI) bus (also known as Mezzanine bus).

The computer system 160 generally comprises a variety of computer readable media. Computer readable media can be any available media that can be accessed by the computer system 160 and includes both volatile and nonvolatile media, removable, and non-removable media. Computer storage media includes volatile and nonvolatile, removable, and non-removable media implemented in any method or technology for storage of information such as computer readable instructions, data structures, program modules, or other data. One or more region-of-operation plots (FIG. 7) may be stored in nonvolatile memory of the computer system 160, for example. Computer storage media includes, but is not limited to, Random Access Memory (RAM), Dynamic RAM (DRAM), Double-Data-Rate DRAM (DDRAM), Synchronous DRAM (SDRAM), Static RAM (SRAM), Programmable ROM (PROM), Read Only Memory (ROM), Electrically Erasable Programmable Read Only Memory (EEPROM), flash memory, polymer memory such as ferroelectric polymer memory, ovonic memory, phase change or ferroelectric memory, silicon-oxide-nitride-oxide-silicon (SONOS) memory, Compact Disk Read Only Memory (CDROM), Compact Disc-rewritable (CDRW) Digital Versatile Disks (DVD) or other optical disk storage, magnetic cassettes, magnetic tape, magnetic disk storage or other magnetic storage devices, or any other medium which can be used to store the desired information and which can be accessed by the computer system 160. It is worthy to note that some portion or the entire computer storage medium may be included in other elements of the computer system 160. For instance, some or all of computer storage medium may be included on the same integrated circuit or chip with elements of the computer system 160 (e.g., processing unit 162). Alternatively, some portion or the entire computer storage medium may be disposed on an integrated circuit or other medium (e.g., a hard disk drive) that is external.

The system memory 164 includes computer storage media in the form of volatile and/or nonvolatile memory such as ROM 168 and RAM 170. A basic input/output system 172 (BIOS), containing the basic routines that help to transfer information between elements within the computer system 160, such as during start-up, is typically stored in the ROM 168. The RAM 170 typically contains data and/or program modules that are immediately accessible to and/or presently being operated on by the processing unit 162. By way of example, and not limitation, FIG. 14 illustrates an operating system 174, one or more application programs 176, other program modules 178, and program data 180.

The computer system 160 also may comprise other removable/non-removable, volatile/nonvolatile computer storage media. By way of example only, FIG. 14 illustrates a hard disk drive 182 that reads data from or writes data to non-removable, nonvolatile magnetic media, a magnetic disk drive 184 that reads data from or writes data to a removable, nonvolatile magnetic disk 186, and an optical disk drive 188 that reads data from or writes data to a removable, nonvolatile optical disk 190, such as a CD ROM, CDRW or other optical media.

Other removable/non-removable, volatile/nonvolatile computer storage media that can be used in the example operating environment include, but are not limited to, magnetic tape cassettes, flash memory cards, digital versatile disks, digital video tape, solid state RAM, solid state ROM, and the like. The hard disk drive 182 is typically connected to the system bus 166 through a non-removable memory interface such as interface 192, and magnetic disk drive 184 and optical disk drive 188 are typically connected to the system bus 166 by a removable memory interface, such as interface 194.

The drives and their associated computer storage media discussed above and illustrated in FIG. 14 provide storage of computer readable instructions, data structures, program modules, and other data for the computer system 160. In FIG. 14, for example, the hard disk drive 182 is illustrated as storing an operating system 196, one or more application programs 198, other program modules 200, and program data 202. Note that these components can either be the same as or different from the operating system 174, the one or more application programs 176, the other program modules 178, and the program data 180. The operating system 196, the one or more application programs 198, the other program modules 200, and the program data 202 are given different numbers here to illustrate that, at a minimum, they are different copies. A user may enter commands and information into the computer system 160 through input devices such as a keyboard 204 and pointing device 206, commonly referred to as a mouse, trackball, or touch pad. Other input devices (not shown) may include a microphone, joystick, game pad, satellite dish, or the like. These and other input devices are often connected to the processing unit 162 through a user input interface 210 that is coupled to the system bus 166, but may be connected by other interface and bus structures, such as a parallel port, game port or a universal serial bus (USB). A display device 212 or other type of display device is also connected to the system bus 166 via an interface, such as a video interface 214, which may in turn communicate with video memory (not shown). In addition to the display device 212, computer systems also may include other peripheral output devices such as speakers 216 and a printer 218, which may be connected through an output peripheral interface 220.

The computer system 160 may operate in a networked or distributed environment using logical connections to one or more remote computers, such as a remote computer 222. The remote computer 222 may be a personal computer, a server, a router, a network PC, a peer device or other common network node, and typically includes many or all of the elements described above relative to the computer system 160, although only a memory storage device 224 has been illustrated in FIG. 14. The logical connections depicted in FIG. 14 include a local area network (LAN) 226 and a wide area network (WAN) 228, but may also include other networks/buses. Such networking environments are commonplace in homes, offices, enterprise-wide computer networks, intranets, and the Internet.

When used in a LAN networking environment, the computer system 160 is connected to the LAN 226 through a network interface or adapter 230. When used in a WAN networking environment, the computer system 160 generally includes a modem 232 or other means for establishing communications over the WAN 228, such as the Internet. The modem 232, which may be internal or external, may be connected to the system bus 166 via the user input interface 210, or other appropriate mechanism. In a networked environment, program modules depicted relative to the computer system 160, or portions thereof, may be stored in the remote memory storage device. By way of example, and not limitation, FIG. 14 illustrates one or more remote application programs 234 as residing on the memory device 224. It will be appreciated that the network connections shown are non-limiting examples and other means of establishing a communications link between the computers may be used.

Various aspects of a non-destructive evaluation and testing system including a charge source and at least one voltage measurement device are disclosed. The charge source may be for generating a charging environment to produce at least one of a voltage profile and a current on an area of dielectric material disposed over a conductive substrate. The area of dielectric material may include a first area containing a subsurface defect. The area of dielectric material may also include a second area that is defect-free. The at least one voltage measurement device may be for outputting voltage measurements at different positions over the area of dielectric material. The voltage measurements over the first area may differ from voltage measurements over the second area to define a voltage differential.

In certain embodiments, the charge source may include any one of an electron gun, an ionizer, a gas, a powder and a first material that is different than the dielectric material to cause electrical charging of the dielectric material when rubbed against the dielectric material.

In certain embodiments, the current may include a steady-state or quasi steady-state current, and the voltage profile may include a steady-state or quasi steady-state voltage profile.

In certain embodiments, the subsurface defect may be caused by a separation between a portion of the dielectric material and the conductive substrate.

In certain embodiments, the at least one voltage measurement device may include a non-contact voltmeter probe.

In certain embodiments, the at least one voltage measurement device may include a plurality of voltage measurement devices.

In certain embodiments, the charge source may generate a charging environment based on physical properties of the dielectric material such that a breakdown strength of the dielectric material is not exceeded.

In certain embodiments, the system may include at least one processor in communication with at least one computer-readable medium. The at least one computer-readable medium may include instructions for causing the at least one processor to at least one of monitor an operating parameter of the system and control the operating parameter of the system.

In certain embodiments, the at least one processor may control an operating parameter of the charge source.

In certain embodiments, the charge source may emit a charging current; and the at least one processor may control the charge source based on at least one predetermined combination of charging current density and energy that is non-damaging to the dielectric material.

In certain embodiments, the at least one processor may receive the measurements from the voltage measurement device and analyze the received measurements to detect the voltage differential.

In certain embodiments, the at least one processor may receive positional feedback from one or more position sensors to indicate positions of the measurements over the area of dielectric material, and determine a position of the voltage differential on the area of dielectric material based on the received positional feedback.

In certain embodiments, the system may include at least one actuator to control a position of the voltage measurement device relative to the area of dielectric material in response to a positioning signal received by the at least one actuator from the at least one processor.

Methods that may be used to perform, for example, nondestructive evaluation and testing, are also disclosed. One such method may include, in one embodiment, generating a charging environment to produce at least one of a voltage profile and a current on an area of dielectric material disposed over a conductive substrate. The area of dielectric material may include a first area containing a subsurface defect. The area of dielectric material may also include a second area that is defect-free. The method may include measuring voltages over the area of dielectric material at different positions using at least one voltage measurement device. The voltage measurements over the first area may differ from voltage measurements over the second area to define a voltage differential.

In certain embodiments, the method may include controlling a charge source to generate the charging environment such that a breakdown strength of the dielectric material is not exceeded.

In certain embodiments, the method may include controlling the charge source to generate the charging environment based on at least one predetermined combination of charging current density and energy that is non-damaging to the dielectric material.

In certain embodiments, the current may include a steady-state or quasi steady-state current, and the voltage profile may include a steady-state or quasi steady-state voltage profile.

In certain embodiments, the method may include measuring voltages over the area of dielectric material using a non-contact voltmeter probe.

In certain embodiments, the method may include analyzing the measured voltages to detect the voltage differential.

In certain embodiments, the method may include receiving positional feedback to indicate positions of the measurements over the area of dielectric material, and determining a position of the voltage differential on the area of dielectric material based on the received positional feedback.

Another method may include, in one embodiment, producing a voltage differential between a first area of a dielectric material and a second area of the dielectric material by using a charge source. The dielectric material may be disposed over a conductive substrate. The first area of the dielectric material may be delaminated from the conductive substrate and the second area of the dielectric material may not be delaminated from the conductive substrate. The method may also include determining a position of the first area of dielectric material by determining a position of the voltage differential.

In certain embodiments, the method may include determining a position of the voltage differential by scanning the dielectric material using a non-contact voltmeter probe.

In certain embodiments, the method may include determining at least one combination of charging current density and energy that is non-damaging to the dielectric material, and controlling the charge source in accordance with the at least one combination of charging current density and energy.

Reference throughout the specification to "various embodiments," "some embodiments," "one embodiment," "an embodiment," and the like means that a particular feature, structure, or characteristic described in connection with the embodiment is included in at least one embodiment. Thus, appearances of the phrases "in various embodiments," "in some embodiments," "in one embodiment," "in an embodiment," and the like in places throughout the specification are not necessarily all referring to the same embodiment. Furthermore, the particular features, structures, or characteristics may be combined in any suitable manner in one or more embodiments. Thus, the particular features, structures, or characteristics illustrated or described in connection with one embodiment may be combined, in whole or in part, with the features, structures, or characteristics of one or more other embodiments without limitation.

The examples presented herein are intended to illustrate potential and specific implementations of the embodiments. It can be appreciated that the examples are intended primarily for purposes of illustration for those skilled in the art. No particular aspect or aspects of the examples is/are intended to limit the scope of the described embodiments. The figures and descriptions of the embodiments have been simplified to illustrate elements that are relevant for a clear understanding of the embodiments, while eliminating, for purposes of clarity, other elements.

While various embodiments have been described herein, it should be apparent that various modifications, alterations, and adaptations to those embodiments may occur to persons skilled in the art with attainment of at least some of the advantages. The disclosed embodiments are therefore intended to include all such modifications, alterations, and adaptations without departing from the scope of the embodiments as set forth herein.

What is claimed is:

1. A system, comprising:
    a charge source for generating a charging environment to produce at least one of a steady-state or quasi steady-state voltage profile and a steady-state or quasi steady-state current on an area of dielectric material disposed over a substrate, wherein the area of dielectric material comprises a first area containing a subsurface defect, and wherein the area of dielectric material comprises a second area that is defect-free; and
    at least one voltage measurement device for outputting voltage measurements at different positions over the area of dielectric material, wherein voltage measurements over the first area differ from voltage measurements over the second area to define a voltage differential.

2. The system of claim 1, wherein the charge source comprises any of: an electron gun, an ionizer, a gas, a powder, a first material that is different than the dielectric material to cause electrical charging of the dielectric material when rubbed against the dielectric material.

3. The system of claim 1, wherein the subsurface defect is caused by a separation between a portion of the dielectric material and the substrate.

4. The system of claim 1, wherein the at least one voltage measurement device comprises a non-contact voltmeter probe.

5. The system of claim 1, wherein the at least one voltage measurement device comprises a plurality of voltage measurement devices.

6. The system of claim 1, wherein the charge source is for generating a charging environment based on physical properties of the dielectric material such that a breakdown strength of the dielectric material is not exceeded.

7. The system of claim 1, comprising at least one processor in communication with at least one computer-readable medium, wherein the at least one computer-readable medium comprises instructions for causing the at least one processor to at least one of: monitor an operating parameter of the system and control the operating parameter of the system.

8. The system of claim 7, wherein the at least one processor is to control an operating parameter of the charge source.

9. The system of claim 8, wherein the charge source emits a charging current, and wherein the at least one processor is to control the charge source based on at least one predetermined combination of charging current density and energy that is non-damaging to the dielectric material.

10. The system of claim 7, wherein the at least one processor is to:
receive the measurements from the voltage measurement device; and
analyze the received measurements to detect the voltage differential.

11. The system of claim 10, wherein the at least one processor is to:
receive positional feedback from one or more position sensors to indicate positions of the measurements over the area of dielectric material; and
determine a position of the voltage differential on the area of dielectric material based on the received positional feedback.

12. The system of claim 7, comprising at least one actuator to control a position of the voltage measurement device relative to the area of dielectric material in response to a positioning signal received by the at least one actuator from the at least one processor.

13. A method, comprising:
generating with a charge source a charging environment to produce at least one of a steady-state or quasi steady-state voltage profile and a steady-state or quasi steady-state current on an area of dielectric material disposed over a substrate, wherein the area of dielectric material comprises a first area containing a subsurface defect, and wherein the area of dielectric material comprises a second area that is defect-free; and
measuring voltages over the area of dielectric material at different positions using at least one voltage measurement device, wherein voltage measurements over the first area differ from voltage measurements over the second area to define a voltage differential.

14. The method of claim 13, comprising controlling the charge source to generate the charging environment such that a breakdown strength of the dielectric material is not exceeded.

15. The method of claim 14, comprising controlling the charge source to generate the charging environment based on at least one predetermined combination of charging current density and energy that is non-damaging to the dielectric material.

16. The method of claim 14, comprising controlling the charge source based on a dependency of the charge source on one or more experimentally-determined operating parameters of the charge source.

17. The method of claim 13, comprising measuring voltages over the area of dielectric material using a non-contact voltmeter probe.

18. The method of claim 13, comprising:
analyzing the measured voltages to detect the voltage differential.

19. The method of claim 18, comprising:
receiving positional feedback to indicate positions of the measurements over the area of dielectric material; and
determining a position of the voltage differential on the area of dielectric material based on the received positional feedback.

20. A method, comprising:
producing a voltage differential between a first area of a dielectric material and a second area of the dielectric material by using a charge source, wherein the dielectric material is disposed over a substrate, and wherein the first area of the dielectric material is delaminated from the substrate and the second area of the dielectric material is not delaminated from the substrate; and
determining a position of the first area of dielectric material by determining a position of the voltage differential; determining at least one combination of charging current density and energy that is non- damaging to the dielectric material; and controlling the charge source in accordance with the at least one combination of charging current density and energy.

21. The method of claim 20, comprising determining a position of the voltage differential by scanning the dielectric material using a non-contact voltmeter probe.

22. A system, comprising:
a charge source for generating a charging environment to produce at least one of a voltage profile and a current on an area of dielectric material disposed over a substrate, wherein the area of dielectric material comprises a first area containing a subsurface defect, and wherein the area of dielectric material comprises a second area that is defect-free, and wherein the charge source emits a charging current;
at least one voltage measurement device for outputting voltage measurements at different positions over the area of dielectric material, wherein voltage measurements over the first area differ from voltage measurements over the second area to define a voltage differential; and
at least one processor in communication with at least one computer-readable medium, wherein the at least one computer-readable medium comprises instructions for causing the at least one processor to control an operating parameter of the charge source based on at least one predetermined combination of charging current density and energy that is non-damaging to the dielectric material.

23. A system, comprising:
a charge source for generating a charging environment to produce at least one of a voltage profile and a current on an area of dielectric material disposed over a substrate, wherein the area of dielectric material comprises a first area containing a subsurface defect, and wherein the area of dielectric material comprises a second area that is defect-free;
at least one voltage measurement device for outputting voltage measurements at different positions over the area of dielectric material, wherein voltage measurements over the first area differ from voltage measurements over the second area to define a voltage differential; and
at least one processor in communication with at least one computer-readable medium, wherein the at least one computer-readable medium comprises instructions for causing the at least one processor to:
at least one of monitor an operating parameter of the system and control the operating parameter of the system;
receive the measurements from the voltage measurement device;
analyze the received measurements to detect the voltage differential;
receive positional feedback from one or more position sensors to indicate positions of the measurements over the area of dielectric material; and
determine a position of the voltage differential on the area of dielectric material based on the received positional feedback.

24. A system, comprising:
- a charge source for generating a charging environment to produce at least one of a voltage profile and a current on an area of dielectric material disposed over a substrate, wherein the area of dielectric material comprises a first area containing a subsurface defect, and wherein the area of dielectric material comprises a second area that is defect-free;
- at least one voltage measurement device for outputting voltage measurements at different positions over the area of dielectric material, wherein voltage measurements over the first area differ from voltage measurements over the second area to define a voltage differential;
- at least one processor in communication with at least one computer-readable medium, wherein the at least one computer-readable medium comprises instructions for causing the at least one processor to at least one of: monitor an operating parameter of the system and control the operating parameter of the system; and
- at least one actuator to control a position of the voltage measurement device relative to the area of dielectric material in response to a positioning signal received by the at least one actuator from the at least one processor.

25. A method, comprising:
- generating a charging environment to produce at least one of a voltage profile and a current on an area of dielectric material disposed over a substrate, wherein the area of dielectric material comprises a first area containing a subsurface defect, and wherein the area of dielectric material comprises a second area that is defect-free;
- measuring voltages over the area of dielectric material at different positions using at least one voltage measurement device, wherein voltage measurements over the first area differ from voltage measurements over the second area to define a voltage differential; and
- controlling the charge source based on a dependency of the charge source on one or more experimentally-determined operating parameters of the charge source.

* * * * *